United States Patent [19]

Rowe et al.

[11] Patent Number: 5,256,810
[45] Date of Patent: Oct. 26, 1993

[54] METHOD FOR ELIMINATING NITRIDING DURING ACRYLONITRILE PRODUCTION

[75] Inventors: Steven J. Rowe; John T. Shultz, both of Medina; Robert J. Mack, Elida, all of Ohio; Susan L. Dio, Port Lavaca, Tex.

[73] Assignee: The Standard Oil Company, Cleveland, Ohio

[21] Appl. No.: 960,653

[22] Filed: Oct. 14, 1992

[51] Int. Cl.$^5$ .................................. C07C 253/26
[52] U.S. Cl. .............................. 558/320; 558/321; 558/322; 558/323; 558/324; 558/325; 558/326
[58] Field of Search ............... 558/320, 321, 322, 323, 558/324, 325, 326

[56] References Cited

U.S. PATENT DOCUMENTS

| 3,254,110 | 5/1966 | Sennewald et al. | 260/465.3 |
|---|---|---|---|
| 3,472,892 | 10/1969 | Callahan et al. | 260/465.3 |
| 3,639,103 | 2/1972 | Sheely | 558/326 X |
| 3,642,930 | 2/1972 | Grasselli et al. | 558/324 X |
| 3,704,690 | 12/1972 | Menenkamp | 122/7 R |
| 3,944,592 | 3/1976 | Sheely | 260/465.3 |
| 4,246,191 | 1/1981 | Pujado | 558/321 X |
| 4,305,886 | 12/1981 | Pujado | 558/322 X |
| 4,401,153 | 8/1983 | Marsch et al. | 165/134 R |
| 4,767,878 | 8/1988 | Grasselli et al. | 558/324 |
| 4,801,731 | 1/1989 | Jordan | 558/320 |
| 5,015,756 | 5/1991 | Ramachandran et al. | 558/323 X |
| 5,110,854 | 5/1992 | Ratliff | 524/439 |

FOREIGN PATENT DOCUMENTS 0113524 7/1984 European Pat. Off. .
1265770 3/1972 United Kingdom .

Primary Examiner—Joseph Paul Brust

[57] ABSTRACT

An improved process for substantially eliminating, preferably completely eliminating of nitride formation on feed conduits for fluid bed catalyst reactors used in the manufacture of unsaturated nitriles from corresponding olefins, NH$_3$ and oxygen comprising maintaining the temperature of the ammonia inside the conduit below its dissociation temperature and/or maintaining the temperature of the inside surface of the conduit below the temperature at which any monoatomic nitrogen can react with the conduit to form a nitride.

11 Claims, 1 Drawing Sheet

METHOD FOR ELIMINATING NITRIDING DURING ACRYLONITRILE PRODUCTION

BACKGROUND OF THE INVENTION

This invention relates to an improved process for the preparation of unsaturated nitriles from corresponding unsaturated olefins by the reaction of ammonia, oxygen and the unsaturated olefin in a fluidized bed catalytic reactor. In particular, the invention is directed to an improved process for the preparation of acrylonitrile by the reaction of ammonia, propylene and oxygen in a fluidized bed catalytic reactor.

The direct ammoxidation of an unsaturated olefin to its corresponding unsaturated nitrile in a fluidized bed reactor is well known. In particular, the production of acrylonitrile by the reaction of ammonia, propylene and oxygen using fluidized bed catalytic reactors is a widely practiced commercial process developed and commercialized by the assignees of the present invention and referred to worldwide as the Sohio Acrylonitrile Process. The process is carried out in a fluidized bed reactor wherein the reactants are passed upwardly through a suitable catalyst and the products and any unreacted starting materials are removed from the top of the reactor. The catalyst used in these processes have been fully described in various U.S. Pat. Nos. 3,642,930; 4,863,891; and 4,767,878 herein incorporated by reference.

A problem associated with the Sohio Acrylonitrile Process has been the nitriding of the feed conduits used to introduce the amrionia into the fluidized bed reactor. It has been observed that over the passage of time, the ammonia feed conduits for the fluidized bed reactor are subject to nitriding (the reaction of monoatomic nitrogen with the metal surface of the feed conduit/sparger) resulting in the metal itself becoming brittle and subject to mechanical failure. This problem has required replacement of the conduits/spargers on a regular basis to maintain the integrity of the apparatus. Over the years, many solutions to the nitriding problems associated with the operation of the Sohio Acrylonitrile Process have been proposed including replacement of the metal conduits or spargers with specific material which is not prone to nitriding. However, this solution has not been completely successful due to other problems associated with the use of nitride resistant material in the environment of the fluidized bed reactor while making acrylonitrile as well as the cost associated with use of these materials.

The problem of nitriding of metals in other environments has been known for many years as evidence by U.S. Pat. Nos. 3,704,690; 4,401,153; 5,110,584; and EPO Patent 0 113 524. These patents each is directed to solutions to the nitriding problem which include the use of nitride resistant alloys. The present invention is directed to a solution to the nitriding problem associated with the Sohio Acrylonitrile Process which does not necessarily incorporate the use of nitriding resistant material.

SUMMARY OF THE INVENTION

The primary object of the present invention is to provide an improved process for the manufacture of acrylonitrile which substantially eliminates the nitriding problem associated with reactor components.

Additional objects and advantages of the invention will be set forth in part in the description which follows and in part will be obvious from the description or may be learned by practice of the invention. The objects and advantages of the invention may be realized and obtained by means of the instrumentalities and embodiments particularly pointed out in the appended claims.

To achieve the forgoing object and other objects and in accordance with the purpose of the present invention as embodied and broadly described herein, the method of the present invention comprises introducing gaseous propylene, ammonia and oxygen into a fluid bed reactor through at least one conduit to react in the presence of a fluid bed catalyst to produce acrylonitrile wherein the improvement comprises maintaining the temperature of the ammonium vapors while inside the conduit below the dissociation temperature of ammonia.

In accordance with an additional aspect of the present invention as embodied and broadly described herein, the method of the present invention comprises a process for the preparation of acrylonitrile comprising introducing gaseous propylene, ammonia and oxygen into a fluid bed reactor through at least one conduit to react in the presence of a fluid bed catalyst to produce acrylonitrile wherein the improvement comprises maintaining the temperature of the inside surface of the conduit which contacts the ammonia gas at a temperature below the temperature at which any dissociated nitrogen can react with the conduit to form a nitride.

In a preferred embodiment of the present invention, the temperature of the ammonia inside the conduit is maintained below the dissociation temperature of ammonia vapors and the inside surface of the conduit is maintained below the temperature at which any dissociated nitrogen can react with the conduit to form a nitride.

In another preferred embodiment of the present invention the feed conduit comprises a sparger.

In a still further preferred embodiment of the present invention, the sparger comprises a header pipe connected to lateral tubes having multiple orifices therein.

In a further preferred embodiment of the present invention, the inside surface of the conduit is maintained at a temperature below which nitriding may occur by providing a blanket of thermal insulation about the outer surface of the conduit.

In a still further preferred embodiment of the present invention, a second conduit is provided about the outside surface of the thermal insulation to provide an abrasion resistant layer for protection of the thermal insulation.

The significance of the process of the present invention is that it provides a simple and economic means for prevention of the nitriding of the surface of the feed conduits in a fluidized bed reactor used for the manufacture of acrylonitrile. The problem of nitriding of the feed conduits or spargers utilized in the fluid bed reactor for acrylonitrile manufacture has been present for many years. Prior attempts at solutions to this nitriding problem have centered upon focusing on utilization of different materials, such as Inconel, which would not form nitrides with the dissociated nitrogen. However, the use of these sophisticated alloys has not been satisfactory.

The present invention recognizes that for nitriding to occur two conditions must exist. First, the ammonia must be at a temperature above that at which it dissociates (forms monoatomic nitrogen and hydrogen) and second, the temperature of the inside surface of the conduit or sparger which carries the ammonia into the reactor must be at a temperature where the nitriding reaction will occur. Applicants have discovered that the temperature of the ammonia while inside the conduit or sparger prior to exit into contact with the fluidized bed catalyst can be maintained below the ammonia dissociation temperature with no adverse affect on the acrylonitrile manufacturing procedure. In addition, applicants have discovered that it is possible to maintain the temperature of the inside surface of the conduit or sparger at below the temperature required for nitriding by a relatively simple means which does not adversely affect the economics of the process. Each of these means can be used separately to substantially eliminate the nitriding problems associated with the manufacture of acrylonitrile. In the preferred embodiment of the present invention, both techniques are utilized simultaneously resulting in the elimination of the necessity for replacing the conduits or spargers over a period of time. This results in a substantial economics savings for manufacturers of acrylonitrile utilizing the Sohio Acrylonitrile Process.

BRIEF DESCRIPTION OF THE DRAWINGS

The accompanying drawings, which is incorporated in and forms a part of the specification, illustrates a preferred embodiment of the present invention, and together with the description serves to explain the principles of the invention.

Figure 1:
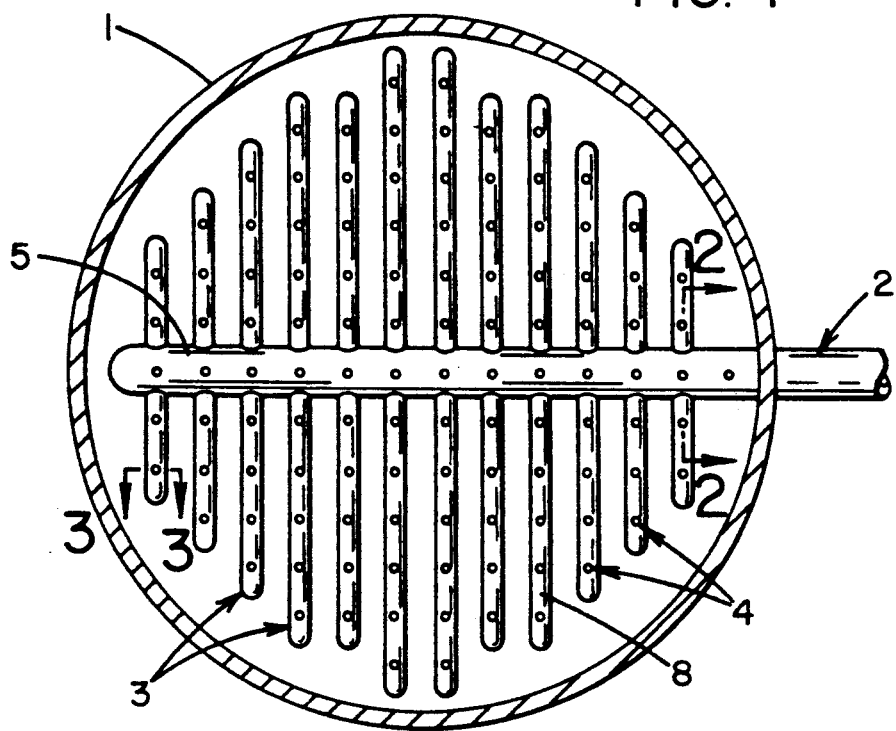
FIG. 1 is a downward cross sectional view of a fluidized bed reactor.

Reference shall now be made in detail for the present preferred embodiment of the invention, example of which is illustrated in the accompanying drawing.

DESCRIPTION OF THE PREFERRED EMBODIMENT

The process of the present invention comprises a method for the manufacture of acrylonitrile comprising introducing gaseous propylene, ammonia and oxygen into a fluid bed reactor through at least one conduit to react in the presence of a fluid bed catalyst to produce acrylonitrile wherein the improvement comprises maintaining the temperature of the ammonium gas while inside the conduit below the dissociation temperature of ammonia. The temperature of dissociation for ammonia is about 150° C.

In another aspect of the present invention, the process of the manufacture of acrylonitrile comprises introducing gaseous propylene, ammonia and oxygen into a fluid bed reactor through at least one conduit to react in the fluid bed reactor in the presence of a fluid bed catalyst to produce acrylonitrile wherein the improvement comprises maintaining the temperature of the inside surface of the conduit through which the ammonia is fed to the reactor below the temperature where any dissociated nitrogen can react with the surface of the conduit to form a nitride. The metal temperature must be above 350° C. for nitride formation to begin.

With reference to the drawing, the process of the present invention will now be described in detail.

FIG. 1 shows a cross sectional view of a typical sparger system for an acrylonitrile reactor. Header 2 is usually comprised of the largest diameter metal pipe which penetrates the reactor 1 and allows ammonia and propylene feeds to enter the reactor. Laterals 3 are the medium sized metal pipe branch connections coming off header 2. Nozzles 4 usually comprising orifices 10 and shrouds 11, come off the laterals 3 over the entire length of laterals 3 to distribute the feed uniformly throughout the reactor 1.

Figure 2:
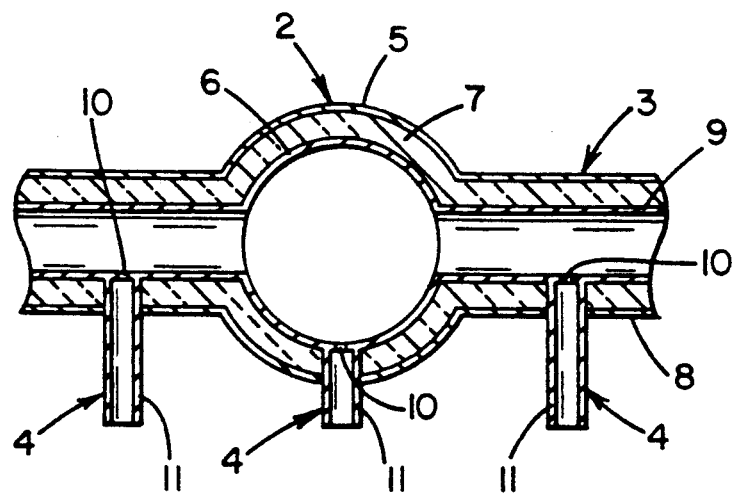
FIG. 2 is a cross section view of a fluidized bed reactor taken along lines A—A of FIG. 1.
Figure 3:
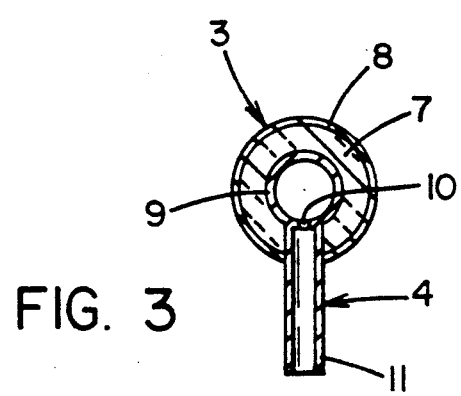
FIG. 3 is a cross section view of a fluidized bed reactor taken along line B—B of FIG. 1.

FIG. 2 and 3 illustrates a preferred embodiment of the present invention. Referring to FIG. 2 shown in header 2 (FIG. 1) comprises a first conduit 5 having a second conduit 6 disposed inside and spaced apart from conduit 5. Conduits 5 and 6 are closed at one end. The space between conduit 5 and 6 is filled with thermal insulation 7 to maintain the inside surface of conduit 6 below the temperature required for metal conduit 6 to react with any monoatomic nitrogen present inside conduit 6 to form a nitride. In FIG. 3, laterals 3 (shown in FIG. 1) also comprises a first conduit 8 and a second conduit 9 wherein conduit 9 is disposed inside conduit 8 and spaced apart from conduit 8. Conduit 8 and 9, similar to conduits 5 and 6, are closed at one end and the space between conduits 8 and 9 is filled with insulation 7 in the same manner as described previously. Orifices 10 are designed in a conventional manner allowing ammonia and propylene to be evenly distributed throughout the fluidized bed reactor 1. In the preferred embodiment, nozzles 4 are comprised of orifices 10 which may include protective shrouds 11 to direct the feed downward into the fluidized bed.

The acrylonitrile reactor shell is made from conventional metal alloys known in the prior art. Typical feed spargers (conduits) are constructed of schedule 40 or 80 seamless carbon or low chromium alloy steel pipe.

In another aspect of the present invention, the shrouds may be made of nitride resistant material such as Inconel, Alonized carbon steel, Alonized low chromium alloy steel, etc. Inconel is especially preferred. These materials may be utilized for the shrouds since they comprise such a small part of the total sparger that the cost associated with use of these materials is not great.

During the process of manufacture of acrylonitrile, ammonia and propylene are fed through header 2 into laterals 3 for dispersion through nozzles 4 into reactor 1. Oxygen in the form of air is injected into the bottom of reactor 1 by conventional means (Not shown). The temperature, ratio of propylene, ammonia and feed rates are all conventional as shown in U.S. Pat. No. 4,801,731 herein incorporated by reference. The temperature of the ammonia inside header 2 and laterals 3 is maintained below the dissociation temperature for ammonia. Accordingly, the ammonia should not and preferably will not dissociate into monoatomic nitrogen and hydrogen thereby substantially eliminating, preferably completely eliminating, the possibility of nitriding to occur on the inside surface of conduit 6 of header 2 and the inside surface of conduit 9 of laterals 3. In addition, the temperature of the inside surface of conduits 6 and 9 is maintained below the temperature required for free nitrogen to react with the metal surface of conduit 6 and 9 to produce a nitride. This is accomplished by blanketing conduits 6 and 9 with a layer of thermal insulation 7 followed by providing second conduits 5 and 8 respectively about conduits 6 and 9 to protect the insulation 7 from abrasion of its surface by the fluidized bed catalyst.

The foregoing description of the preferred embodiment of the invention has been presented for purposes of illustration and description. It is not intended to be exhausted or to limit the invention to the 35 precise form disclosed and obviously many modifications and variations are possible in light of the above teaching. The embodiment was chosen and described in order to best explain the principles of the invention and its practical application to thereby enable others skilled in the art to best utilize the invention in various embodiments and with various modifications as are suitable to the particular use contemplated. It is intended that the scope of the invention be defined with the claims appended hereto.

What we claim is:

1. A method for the production of unsaturated nitrile from the corresponding unsaturated olefin comprising introducing the gaseous olefin, ammonia and oxygen into a fluid bed reactor through at least one conduit to react in the presence of a fluid bed catalyst to produce the corresponding nitrile wherein the improvement comprises maintaining the temperature of the ammonium vapors while inside the conduit below the dissociation temperature of ammonia.

2. The process of claim 1 further comprising maintaining the temperature of the inside surface of said conduit which contacts the ammonia at a temperature below the temperature at which nitrogen can react with said conduit to form a nitride.

3. The process of claim 1 wherein said feed conduit comprises a sparger comprising at least one header pipe connected to at least one lateral tube containing at least one nozzle therein.

4. The process of claim 3 wherein said nozzle further comprises at least one orifice and usually one shroud connected to each said orifice.

5. The process of claim 1 wherein said ammonium vapors while inside said conduit are maintained at a temperature below the dissociation temperature of ammonia by providing a blanket of thermal insulation about the outer surface of the conduit.

6. The process of claim 5 wherein a second conduit is provided about the outside surface of the thermal insulation to provide a protective surface for said thermal insulation.

7. The process of claim 2 wherein said inside surface of said conduit is maintained at a temperature below the temperature at which any dissociated nitrogen can react with said conduit by providing a blanket of thermal insulation about the outer surface of the conduit.

8. The process of claim 7 wherein a second conduit is provided about the outside surface of the thermal insulation to provide a protective surface for said thermal insulation.

9. A process for the preparation of an unsaturated nitrile from the corresponding unsaturated olefin comprising introducing the gaseous olefin, ammonia and oxygen into a fluid bed reactor through at least one conduit to react in the presence of a fluid bed catalyst to produce the corresponding nitrile wherein the improvement comprises maintaining the temperature of the inside surface of the conduit which contacts the ammonia gas at a temperature below the temperature at which any dissociated nitrogen can react with the conduit to form a nitride.

10. The process of claim 9 wherein said inside surface of said conduit is maintained at a temperature below the temperature at which any dissociated nitrogen can react with said conduit by providing a blanket of thermal insulation about the outer surface of the conduit.

11. The process of claim 10 wherein a second conduit is provided about the outside surface of the thermal insulation to provide a protective surface for said thermal insulation.

* * * * *